United States Patent [19]

Troxler et al.

[11] 4,165,374
[45] Aug. 21, 1979

[54] THIENO[3,2-c]PYRIDINES

[75] Inventors: Franz Troxler; Erik Wiskott, both of Bottmingen, Switzerland

[73] Assignee: Sandoz Ltd., Basel, Switzerland

[21] Appl. No.: 922,519

[22] Filed: Jul. 7, 1978

Related U.S. Application Data

[63] Continuation-in-part of Ser. No. 765,233, Feb. 3, 1977, abandoned.

[30] Foreign Application Priority Data

Feb. 9, 1976 [CH] Switzerland ............... 1530/76
Jul. 29, 1977 [CH] Switzerland ............... 9419/77

[51] Int. Cl.² ............... C07D 495/04; A61K 31/44
[52] U.S. Cl. ............... 424/256; 546/114
[58] Field of Search ............... 546/114; 424/256

[56] References Cited

U.S. PATENT DOCUMENTS 3,998,835 12/1976 Troxler et al. ............... 546/114
4,071,630 1/1978 Wiskott et al. ............... 424/256

Primary Examiner—Alan L. Rotman
Attorney, Agent, or Firm—Gerald D. Sharkin; Robert S. Honor

[57] ABSTRACT

This invention provides compounds of formula I

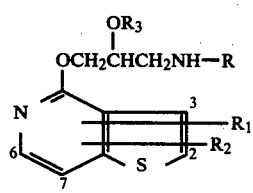

wherein
$R_1$ is
  (i) hydrogen or alkyl of 1 to 4 carbon atoms, or
  (ii) chlorine or bromine, in the 2, 3 or 7 position, or
  (iii) fluorine, cyano or COOB, wherein B is alkyl of 1 to 4 carbon atoms, in the 2 or 3 position, $R_2$ is
  (i) hydrogen or alkyl of 1 to 4 carbon atoms, or
  (ii) chlorine or bromine, in the 2, 3 or 7 position, or
  (iii) fluorine, in the 2 or 3 position, either $R_3$ is a group —$COR_4$, wherein
$R_4$ is alkyl of 1 to 17 carbon atoms, phenyl, phenyl monosubstituted by nitro, phenyl mono- or disubstituted by alkyl of 1 to 4 carbon atoms or halogen with an atomic number of 9 to 35, phenyl mono-, di- or trisubstituted by alkoxy of 1 to 4 carbon atoms, or a group D—COOH, wherein D is ethylene or trimethylene, and
R is phenylalkyl of 8 to 10 carbon atoms, phenylalkyl of 8 to 10 carbon atoms monosubstituted in the phenyl radical by alkyl of 1 to 4 carbon atoms, alkoxy of 1 to 4 carbon atoms or halogen with an atomic number of 9 to 35, or phenylalkyl of 8 to 10 carbon atoms disubstituted in the phenyl radical by alkoxy of 1 to 4 carbon atoms, the phenyl ring of each of the phenylalkyl radicals being separated by at least 2 carbon atoms from the nitrogen atom to which R is bound, alkyl of 3 to 7 carbon atoms, cycloalkyl of 3 to 7 carbon atoms, cycloalkyl of 3 to 7 carbon atoms monosubstituted by alkyl of 1 to 4 carbon atoms, α-dialkylpropinyl of 5 to 9 carbon atoms, α-dialkylallyl of 5 to 9 carbon atoms, or phenoxyalkyl of 8 to 11 carbon atoms, the oxygen atom of the phenoxyalkyl radical being separated by at least two carbon atoms from the nitrogen atom to which R is bound, or
$R_3$ is hydrogen and
R is phenylalkyl of 8 to 10 carbon atoms, phenylalkyl of 8 to 10 carbon atoms monosubstituted in the phenyl radical by alkyl of 1 to 4 carbon atoms, alkoxy of 1 to 4 carbon atoms or halogen with an atomic number of 9 to 35, or phenylalkyl of 8 to 10 carbon atoms disubstituted in the phenyl radical by alkoxy of 1 to 4 carbon atoms, the phenyl ring of each of the phenylalkyl radicals being separaed by at least 2 carbon atoms from the nitrogen atom to which R is bound, with the general proviso that, when $R_1$ is cyano or COOB, $R_2$ is other than fluorine, chlorine or bromine, in the 2 or 3 position, useful in the treatment of heart diseases, hyperlipoidemia and hyperglycemia.

35 Claims, No Drawings

THIENO[3,2-c]PYRIDINES

This application is a continuation-in-part of our co-pending application Ser. No. 765,233 filed Feb. 3, 1977, now abandoned.

The present invention relates to thieno[3,2c]pyridine derivatives.

In accordance with the invention there are provided compounds of formula I,

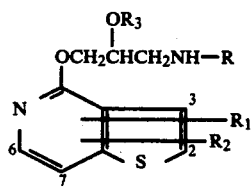

wherein $R_1$ is
- (i) hydrogen or alkyl of 1 to 4 carbon atoms, or
- (ii) chlorine or bromine, in the 2, 3 or 7 position, or
- (iii) fluorine, cyano or COOB, wherein B is alkyl of 1 to 4 carbon atoms, in the 2 or 3 position, $R_2$ is
- (i) hydrogen or alkyl of 1 to 4 carbon atoms, or
- (ii) chlorine or bromine, in the 2, 3 or 7 position, or
- (iii) fluorine, in the 2 or 3 position, either $R_3$ is a group —$COR_4$, wherein $R_4$ is alkyl of 1 to 17 carbon atoms, phenyl, phenyl monosubstituted by nitro, phenyl mono- or disubstituted by alkyl of 1 to 4 carbon atoms or halogen with an atomic number of 9 to 35, phenyl mono-, di- or trisubstituted by alkoxy of 1 to 4 carbon atoms, or a group D—COOH, wherein D is ethylene or trimethylene, and R is phenylalkyl of 8 to 10 carbon atoms, phenylalkyl of 8 to 10 carbon atoms monosubstituted in the phenyl radical by alkyl of 1 to 4 carbon atoms, alkoxy of 1 to 4 carbon atoms or halogen with an atomic number of 9 to 35, or phenylalkyl of 8 to 10 carbon atoms disubstituted in the phenyl radical by alkoxy of 1 to 4 carbon atoms, the phenyl ring of each of the phenylalkyl radicals being separated by at least 2 carbon atoms from the nitrogen atom to which R is bound, alkyl of 3 to 7 carbon atoms, cycloalkyl of 3 to 7 carbon atoms, cycloalkyl of 3 to 7 carbon atoms monosubstituted by alkyl of 1 to 4 carbon atoms, α-dialkylpropinyl of 5 to 9 carbon atoms, α-dialkylallyl of 5 to 9 carbon atoms, or phenoxyalkyl of 8 to 11 carbon atoms, the oxygen atom of the phenoxyalkyl radical being separated by at least two carbon atoms from the nitrogen atom to which R is bound, or $R_3$ is hydrogen and R is phenylalkyl of 8 to 10 carbon atoms, phenylalkyl of 8 to 10 carbon atoms monosubstituted in the phenyl radical by alkyl of 1 to 4 carbon atoms, alkoxy of 1 to 4 carbon atoms or halogen with an atomic number of 9 to 35, or phenylalkyl of 8 to 10 carbon atoms disubstituted in the phenyl radical by alkoxy of 1 to 4 carbon atoms, the phenyl ring of each of the phenylalkyl radicals being separated by at least 2 carbon atoms from the nitrogen atom to which R is bound, with the general proviso that, when $R_1$ is cyano or COOB, $R_2$ is other than fluorine, chlorine or bromine, in the 2 or 3 position.

R is preferably hydrogen, alkyl, chlorine, bromine or cyano, especially cyano. $R_2$ is preferably hydrogen or alkyl, especially hydrogen. $R_3$ is preferably a group —$COR_4$. $R_4$ is preferably alkyl, phenyl, phenyl substituted by halogen, especially chlorine, or by alkoxy, or is a group D—COOH. R is preferably alkyl, alkylcycloalkyl, phenylalkyl or phenylalkyl substituted by alkoxy, especially alkyl.

Alkoxy preferably contains 1 or 2, especially 1 carbon atom. When $R_1$ and/or $R_2$ is alkyl or when $R_4$ is phenyl substituted by alkyl or when R is phenylalkyl substituted in the phenyl radical by alkyl or cycloalkyl substituted by alkyl, or when B is alkyl, these alkyl radicals preferably contain 1 or 2, especially 1 carbon atom. When $R_1$ and/or $R_2$ is fluorine, chlorine or bromine, these radicals are preferably chlorine or bromine, especially bromine. When R is alkyl, this radical preferably is branched, especially in an α-position to the nitrogen atom to which it is bound. Especially preferred alkyl radicals R are isopropyl, tert.butyl, 3-pentyl and tert. pentyl, especially tert. butyl.

When $R_4$ is alkyl, this radical preferably contains 1 to 10, especially 4 to 9 carbon atoms. Especially preferred alkyl radicals $R_4$ are tert.butyl, 3-pentyl, tert. pentyl and n-octyl, especially tert. butyl and n-octyl. Halogen of atomic number from 9 to 35 preferably signifies fluorine or chlorine. Phenylalkyl preferably signifies phenethyl, substituted phenylalkyl preferably signifies substituted phenethyl. Cycloalkyl preferably is of 3, 5 or 6, especially of 3 carbon atoms. In cycloalkyl substituted by alkyl, the alkyl radical preferably is attached to the 1 position of the cycloalkyl radical. In α-dialkylpropinyl and α-dialkylallyl, the alkyl radicals preferably are identical and preferably are of 1 or 2, especially of 1 carbon atom. Phenoxyalkyl preferably signifies phenoxyethyl, D is preferably ethylene.

$R_1$ and/or $R_2$ preferably is in the 2 or 3 position. When R is monosubstituted phenylalkyl and/or $R_4$ is monosubstituted phenyl, the phenyl radical preferably is substituted in the 4 position. When R is polysubstituted phenylalkyl and/or $R_4$ is polysubstituted phenyl, the substituents of the phenyl radical may have independent significances, are however preferably identical, and preferably are alkoxy groups, especially in the 3,4 or 3,4,5 positions.

In accordance with the invention, a compound of formula I may be obtained by a process comprising (a) for the production of a compound of formula Ia

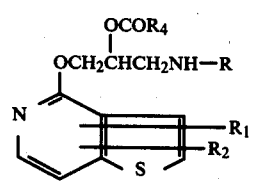

wherein R, $R_1$, $R_2$ and $R_4$ are as defined above, esterifying a compound of formula Ib

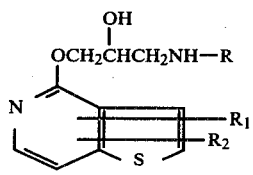

wherein R, $R_1$ and $R_2$ are as defined above, or (b) for the production of a compound of formula Ib, substituting a compound of formula II

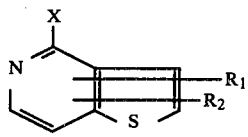

wherein $R_1$ and $R_2$ are as defined above and X is a leaving group, with a group of formula III

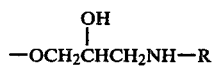

wherein R is as defined above.

Process variant (a) may be effected in a manner analogous to methods known for the acylation of secondary alkohols.

To a compound of formula Ib there may, for example, be added an excess of an anhydride corresponding to the acid of formula $R_3COOH$, as well as an acid. The added acid may be the acid $R_3COOH$, but may however be different. The process may be effected from about 0° to about 100° C., preferably from about room temperature to about 40° C. The process is optionally effected in the presence of an inert organic solvent. The reaction mixture may be worked up in known manner, conveniently under mild conditions, as otherwise the ester group may be split off.

Process variant (b) is a substitution reaction on an aromatic, nitrogen-containing heterocycle which contains a leaving group on a carbon atom adjacent to the nitrogen. It may be effected in a manner analogous to known methods. X preferably signifies an anionic leaving group, e.g. chlorine, bromine or methylthio; X especially signifies chlorine. The substitution is readily effected, e.g. by allowing to stand a solution of a compound of formula II and a compound of formula H—$R_x$, wherein $R_x$ is the group of formula III. This may be effected in an inert organic solvent, e.g. a lower alkanol such as tert.butanol. The reaction is preferably effected in the presence of a base, e.g. an alkali metal alcoholate such as potassium tert.butylate. The reaction temperature may vary from about 0° to about 80° C., and is preferably room temperature.

The carbon atom of the side chain carrying the —$OR_3$ group in the compounds of formula I is asymmetric; the compounds may therefore appear in the form of the corresponding enantiomers.

The individual optical isomers of the compounds of formula I may be obtained in conventional manner, e.g. by effecting the processes according to the invention starting from the corresponding optical isomers of the starting materials, which may be obtained in conventional manner starting from optically pure (R)-or(S)-glyceraldehyde.

The compounds of formula I may be present in the free form, or in the form of acid addition salts. Acid addition salts, for example, the hydrogen maleinate, may be produced from the free compounds in known manner, and vice versa.

Insofar as the production of the starting materials is not described, these are known or may be produced in accordance with known processes, or in a manner analogous to the processes described herein or to known processes.

In the following non-limitative Examples all temperatures are indicated in degrees Centigrade and are uncorrected.

EXAMPLE 1

4-(3-tert.butylamino-2-nonanoyloxypropoxy)-thieno[3,2-c]pyridine-3-carbonitrile [process variant a]

2.7 g of pelargonic acid and 1.3 g 4-(3-tert.butylamino-2-hydroxypropoxy)thieno[3,2-c]pyridine-3-carbonitrile in 12 ml of chloroform are reacted dropwise at 0° with 1.5 g pelargonic anhydride in 3 ml of chloroform. After 15 hours at room temperature, 50 ml of a 2N soda solution are added and the reaction mixture is extracted thrice with methylene chloride, dried over MgSO$_4$, filtered and concentrated. The title compound is formed (M.P. of the hydrogen maleinate form 105°–107°—from tetrahydrofuran).

EXAMPLE 2

{1-tert.butylamino-3-(3-cyano-thieno[3,2-c]pyridine-4-yloxy)-2-propyl}hydrogen succinate [process variant a]

1 g of 4-(3-tert.butylamino-2-hydroxypropoxy)-thieno[3,2-c]pyridine-3-carbonitrile hydrogen maleinate are dissolved in 15 ml acetic acid and reacted at room temperature with 0.48 g of succinic anhydride. After 15 hours 50 ml of ether are added. The hydrogen maleinate of the titel compound is obtained (M.P. 134°–137°).

The following compounds of formula Ia are obtained according to process variant (a) in a manner analogous to Example 1, using the corresponding starting materials of formula Ib:

| Ex. nr. | R | $R_1$ | $R_2$ | $R_4$ | M.P. |
|---|---|---|---|---|---|
| 3 | tert-butyl | 3-bromo | H | phenyl | hml 198°–201° |
| 4 | tert-butyl | 3-bromo | H | tert-butyl | hml 185°–187° |
| 5 | tert-butyl | 2-cyano | H | tert-butyl | hml 169°–172° |
| 6 | tert-butyl | 3-cyano | H | phenyl | hml 202°–204° |
| 7 | tert-butyl | 6-methyl | H | tert-butyl | hml 188°–190° |
| 8 | tert-butyl | 3-bromo | 2-methyl | tert-butyl | hml 160°–163° |
| 9 | tert-butyl | 3-bromo | 2-methyl | 3,4,5-tri-methoxy-phenyl | |
| 10 | tert-butyl | 3-cyano | H | tert-butyl | hml 158°–160° |
| 11* | tert-butyl | 3-cyano | H | 4-fluoro-phenyl | hml 172°–174° |
| 12 | tert-butyl | 3-bromo | 2-methyl | phenyl | hml 197°–200° |
| 13 | tert-butyl | 3-cyano | H | 3,4,5-tri-methoxy-phenyl | hml 207°–210° |
| 13a | tert-butyl | 3-cyano | H | 4-chloro-phenyl | hmo 174°–175° |
| 13b | tert-butyl | 3-cyano | H | 3-chloro-phenyl | hml 92°–94° |

*using as solvent a 1:1 mixture chloroform/hexamethyl-phosphoric acid triamide in place of chloroform
hml = hydrogen maleinate
hmo = hydrogen malonate

EXAMPLE 14

4-[3-(3,4-dimethoxy-phenethylamino)-2-hydroxypropoxy]thieno[3,2-c]pyridine-2-carbonitrile [process variant b]

To a solution of 1.0 g of potassium in 60 ml of tert. butanol produced at 35° is added a solution of 6.4 g of 1,2-dihydroxy-3-(3,4-dimethoxyphenethylamino)propane in 50 ml of tert.butanol; then 5.0 g of 4-chlorothieno[3,2-c]pyridine-2-carbonitrile is added to the mixture. After 4 hours at 30° the reaction mixture is worked up in the usual manner. The title compound is obtained (M.P. of the hydrogen maleinate: 150°–153°).

tional stress. This is indicated in standard tests for showing inhibition of the increase in free fatty acid concentration in blood due to mobilisation and lipolysis, for example in vitro, by an inhibition of glycerol release stimulated by isoproterenol in fat cells of the epididymal fat tissue of rats. This effect is observed at a concentration of about 0.1 to about 10 mg/l solution of the compounds. The cells were isolated in accordance with the method of M. Rodbell [J. Biol. Chem. 239 (1964) 375–380].

For the above-mentioned uses for stress conditions the dosage will, of course, vary depending on the compound employed, made of administration and treatment

| Ex. Nr. | R | $R_1$ | $R_2$ | $R_4$ |
|---|---|---|---|---|
| 15 | —(CH$_2$)$_3$—phenyl | 2-Br | 7-Br | —CH$_3$ |
| 16 | —CH$_2$—CH(CH$_3$)—phenyl—CH$_2$CH$_3$ | H | H | —(CH$_2$)$_{16}$—CH$_3$ |
| 17 | —(CH$_2$)$_3$—phenyl—Cl | 3-F | H | phenyl—NO$_2$ |
| 18 | cyclopropyl | 2-COOC(CH$_3$)$_3$ | H | phenyl—CH$_2$CH$_3$ |
| 19 | cycloheptyl | 2-CH$_2$CH$_3$ | 7-CH$_3$ | Cl—phenyl—Br |
| 20 | cyclopentyl(CH$_2$CH$_3$) | 2-Cl | 3-Cl | —(CH$_2$)$_3$COOH |
| 21 | —C(C$_2$H$_5$)$_2$C≡CH | 6-CH$_3$ | 7-CH$_3$ | phenyl—OCH$_2$CH$_3$ |
| 22 | —C(CH$_3$)$_2$CH=CH$_2$ | 2-F | 6-CH$_3$ | —(CH$_2$)$_{12}$—CH$_3$ |
| 23 | —C(CH$_3$)$_2$CH$_2$O—phenyl | H | H | CH$_3$—phenyl—Cl |

The following compounds of formula Ib are obtained in a manner analogous to Example 14:

| Ex. Nr. | R | $R_1$ | $R_2$ |
|---|---|---|---|
| 24 | —(CH$_2$)$_3$—phenyl—(CH$_2$)$_2$CH$_3$ | H | H |
| 25 | —(CH$_2$)$_3$—phenyl—Cl | 2-CH$_2$CH$_3$ | 3-Cl |
| 26 | —(CH$_2$)$_2$CH(CH$_3$)—phenyl | 2-F | H |
| 27 | —(CH$_2$)$_4$—phenyl | 7-Br | H |
| 28 | —(CH$_2$)$_3$—phenyl(OCH$_2$CH$_3$) | 3-COOC(CH$_3$)$_3$ | H |

The compounds of formula I are useful because they possess pharmacological activity in animals. In particular, the compounds of formula I are useful as inhibitors of hyperlipoidemia and hyperglycemia induced by emotional stress.

desired. However, in general, satisfactory results are obtained with a daily dosage of form about 0.01 to about 5 mg/kg animal body weight, conveniently given in divided doses 2 to 4 times a day, or in sustained release form. For the larger mammal, the total daily dosage is in the range of from about 1 to about 200 mg, and dosage forms suitable for oral administration comprise from about 0.25 to about 100 mg of the compounds admixed with a solid or liquid pharmaceutical carrier or diluent.

Additionally the compounds of formula I are useful as adrenergic β-blocking agents, e.g. for the prophylaxis and therapy of coronary diseases, particularly in the treatment of Angina pectoris, in the hyperkinetic heart syndrome and conditions resulting from muscular hypertrophic subvalvular aortic stenosis, and also as antiarrhythmic agents, e.g. for the treatment of heart rhythm disorders, as indicated in standard tests, e.g. by an inhibition of the positive inotropic—adrenaline effect in the spontaneously beating guinea pig atrium at a bath concentration of from 0.005 to 2.5 mg/litre, in accordance with the method of K. Sammeli, Helv. Phyiol. Acta. 25 CR 215–221 (1967), and an inhibition of the tachycardia and hypotension caused by isoproterenol in the infusion test in the anasthetized dog at an effective cummulative dose of from 0.02 to 0.6 mg/kg animal body weight, administered intravenously.

For the above mentioned uses as adrenergic β-blocking and anti-arrhythmic agents the dosage will, of course, vary depending on the compound employed, mode of administration and treatment desired. However, in general, satisfactory results are obtained with a daily dosage of from about 0.01 to 1.5 mg/kg animal body weight, conveniently given in divided doses 2 to 4 times a day or in sustained release form. For the larger mammal, the total daily dosage is in the range from about 1 to about 100 mg and dosage forms suitable for oral administration comprise from about 0.25 to about 50 mg of the compounds admixed with a solid or liquid pharmaceutical carrier or diluent.

Especially interesting is the adrenergic β-blocking activity of the compounds of formula I.

The S enantiomers of the compounds of formula I are pharmacologically more active than the corresponding R enantiomers.

Preferred compounds of formula Ia are compounds of formula Iaa

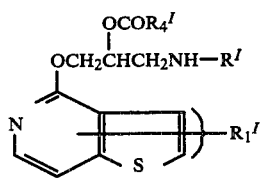

Iaa wherein
$R_1^I$ is hydrogen or alkyl of 1 to 4 carbon atoms, bromine or cyano, in the 2 or 3 position,
$R_4^I$ is alkyl of 4 to 9 carbon atoms, phenyl, phenyl monosubstituted by halogen of atomic number from 9 to 35, phenyl mono-, di- or trisubstituted by alkoxy of 1 to 4 carbon atoms, or a group $D^I$ —COOH, wherein $D^I$ is ethylene, and
$R^I$ is alkyl of 3 to 5 carbon atoms or cycloalkyl of 3,5 or 6 carbon atoms monosubstituted by alkyl of 1 or 2 carbon atoms.

Especially preferred are those compounds of formula Iaa, which are substituted by cyano in the 2- or 3-position, those, which have a tert.butyl radical attached to the nitrogen atom of the side chain and those, wherein $R_4^I$ is alkyl of 4 to 8 carbon atoms, preferably tert. butyl or n-octyl, or $R_4^I$ is phenyl or phenyl mono-substituted by fluorine, preferably in the 4 position. Most especially preferred are 4-(3-tert.butylamino-2-pivaloyloxypropoxy)thieno[3,2-c]pyridine-2-carbonitrile, 4-(3-tert.butylamino-2-nonanoyloxypropoxy)thieno[3,2-c]pyridine-3-carbonitrile, {1-tert.butylamino-3-(3-cyanothieno[3,2-c]pyridine-4-yloxy)-2-propyl}hydrogen succinate and 4-(3-tert.butylamino-2-(p-fluorobenzoyloxy)-propoxythieno[3,2-c]pyridine-3-carbonitrile.

Preferred compounds of formula Ib are compounds of formula Ibb,

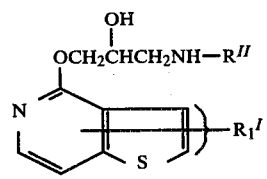

Ibb wherein $R_1^I$ is as defined above and
$R^{II}$ is alkyl of 3 to 5 carbon atoms, cycloalkyl of 3 to 5 carbon atoms monosubstituted by alkyl of 1 or 2 carbon atoms, phenylalkyl of 8 to 10 carbon atoms or phenylalkyl of 8 to 10 carbon atoms mono- or disubstituted in the phenyl radical by alkoxy of 1 or 2 carbon atoms Especially preferred are those compounds of formula Ibb, which are substituted by cyano in the 2- or 3-position, those, which have attached to the nitrogen atom of the side chain a phenylalkyl group of 8 to 10 carbon atoms disubstituted in the phenyl radical by alkoxy of 1 or 2 carbon atoms, preferably disubstituted in the 3 and 4 positions. Most especially preferred is 4-[3-(3,4-dimethoxyphenethylamino)-2-hydroxypropoxy]thieno[3,2-c]pyridine-2-carbonitrile.

The compounds of formula I may be administered in free form or in pharmaceutically acceptable acid addition salt form. Such salt forms exhibit the same order of activity as the free forms and are readily prepared in conventional manner. The present invention also provides a pharmaceutical composition comprising a compound of formula I, in free form or in pharmaceutically acceptable acid addition salt form, in association with a pharmaceutical carrier or diluent. Such compositions may be in the form of, for example, a solution or a tablet.

We claim:
1. A compound of formula I

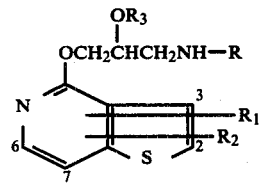

I wherein
$R_1$ is
 (i) hydrogen or alkyl of 1 to 4 carbon atoms, or
 (ii) chlorine or bromine, in the 2,3 or 7 position, or
 (iii) fluorine, cyano or COOB, wherein B is alkyl of 1 to 4 carbon atoms, in the 2 or 3 position,
$R_2$ is
 (i) hydrogen or alkyl of 1 to 4 carbon atoms, or
 (ii) chlorine or bromine, in the 2,3 or 7 position, or
 (iii) fluorine, in the 2 or 3 position, either
$R_3$ is a group —COR$_4$, wherein
$R_4$ is alkyl of 1 to 17 carbon atoms, phenyl, phenyl monosubstituted by nitro, phenyl mono- or disubstituted by alkyl of 1 to 4 carbon atoms or halogen with an atomic number of 9 to 35, phenyl mono-, di- or trisubstituted by alkoxy of 1 to 4 carbon atoms, or a group D—COOH, wherein D is ethylene or trimethylene, and
R is phenylalkyl of 8 to 10 carbon atoms, phenylalkyl of 8 to 10 carbon atoms monosubstituted in the phenyl radical by alkyl of 1 to 4 carbon atoms, alkoxy of 1 to 4 carbon atoms or halogen with an atomic number of 9 to 35, or phenylalkyl of 8 to 10 carbon atoms disubstituted in the phenyl radical by alkoxy of 1 to 4 carbon atoms, the phenyl ring of each of the phenylalkyl radicals being separated by at least 2 carbon atoms from the nitrogen atom to which R is bound, alkyl of 3 to 7 carbon atoms, cycloalkyl of 3 to 7 carbon atoms, cycloalkyl of 3 to 7 carbon atoms monosubstituted by alkyl of 1 to 4 carbon atoms, α-dialkylpropinyl of 5 to 9 carbon atoms, α-dialkylallyl of 5 to 9 carbon atoms, or phenoxyalkyl of 8 to 11 carbon atoms, the oxygen atom of the phenoxyalkyl radical being separated by at least two carbon atoms from the nitrogen atom to which R is bound, or R₃ is hydrogen and R is phenylalkyl of 8 to 10 carbon atoms, phenylalkyl of 8 to 10 carbon atoms monosubstituted in the phenyl radical by alkyl of 1 to 4 carbon atoms, alkoxy of 1 to 4 carbon atoms or halogen with an atomic number of 9 to 35, or phenylalkyl of 8 to 10 carbon atoms disubstituted in the phenyl radical by alkoxy of 1 to 4 carbon atoms, the phenyl ring of each of the phenylalkyl radicals being separated by at least 2 carbon atoms from the nitrogen atom to which R is bound, with the general proviso that, when $R_1$ is cyano or COOB, $R_2$ is other than fluorine, chlorine or bromine, in the 2 or 3 position, or a pharmaceutically acceptable acid addition salt form thereof.

2. A compound of claim 1 in (S)-enantiomeric form.

3. A compound of claim 1 in (R)-enantiomeric form.

4. A compound of claim 1 in racemic form.

5. A compound of claim 1, wherein $R_1$ is hydrogen, chlorine, bromine, cyano or alkyl and $R_2$ is hydrogen or alkyl.

6. A compound of claim 1, wherein $R_4$ is —CH₂—CH₂—COOH.

7. A compound of claim 1, wherein $R_4$ and R are, independently, alkyl.

8. A pharmaceutical composition useful in treating hyperlipoidemia comprising in unit dosage form from about 0.25 milligrams to about 100 milligrams of a compound of claim 1 in association with a pharmaceutically acceptable diluent or carrier.

9. A method of treating coronary diseases, in animals, which comprises administering to an animal in need of such treatment a therapeutically effective amount of a compound of claim 1.

10. A compound of claim 1, wherein $R_4$ is a group D—COOH.

11. A compound of claim 1, wherein $R_4$ is alkyl, phenyl or substituted phenyl.

12. A compound of claim 1, wherein R is tert. butyl, $R_1$ is 3-cyano, $R_2$ is hydrogen and $R_4$ is 4-chlorophenyl.

13. A compound of claim 1, wherein R is tert. butyl, $R_1$ is 3-cyano, $R_2$ is hydrogen and $R_4$ is 3-chlorophenyl.

14. A compound of claim 1, wherein R is alkyl branched in an α-position to the nitrogen atom to which it is bound, $R_1$ is cyano, $R_2$ is hydrogen and $R_4$ is phenyl substituted by halogen.

15. A method of treating heart rythym disorders in animals, which comprises administering to an animal in need of such treatment a therapeutically effective amount of a compound of claim 1.

16. A method of treating hyperlipoidemia in animals, which comprises administering to an animal in need of such treatment a therapeutically effective amount of a compound of claim 1.

17. A method of treating hyperglycemia in animals, which comprises administering to an animal in need of such treatment a therapeutically effective amount of a compound of claim 1.

18. A compound of claim 1 wherein $R_3$ represents COR₄.

19. A compound of the formula

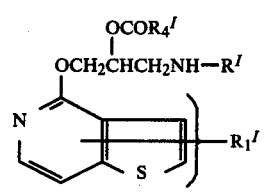

wherein $R_1^I$ is hydrogen or alkyl of 1 to 4 carbon atoms, bromine or cyano, in the 2 or 3 position, $R_4^I$ is alkyl of 4 to 9 carbon atoms, phenyl, phenyl monosubstituted by halogen of atomic number from 9 to 35, phenyl mono-, di- or trisubstituted by alkoxy of 1 to 4 carbon atoms, or a group $D^I$—COOH, wherein $D^I$ is ethylene, and $R^I$ is alkyl of 3 to 5 carbon atoms or cycloalkyl of 3, 5, or 6 carbon atoms monosubstituted by alkyl of 1 or 2 carbon atoms.

20. A compound of claim 19 which is substituted by cyano in the 2- or 3-position.

21. A compound of claim 19 wherein $R_1^I$ represents tert.butyl.

22. The compound of claim 1 which is {1-tert.butylamino-3-(3-cyano-thieno[3,2-c]pyridine-4-yloxy)-2-propyl} hydrogen succinate.

23. The compound of claim 1 which is 4-(3-tert.butylamino-2-nonanoyloxy-propoxy)thieno[3,2-c]pyridine-3-carbonitrile.

24. The compound of claim 18 wherein R represents tert.butyl, $R_1$ represents 3-bromo, $R_2$ represents H, and $R_4$ represents phenyl.

25. The compound of claim 18 wherein R represents tert.butyl, $R_1$ represents 3-bromo, $R_2$ represents H and $R_4$ represents tert.butyl.

26. The compound of claim 18 wherein R represents tert.butyl, $R_1$ represents 2-cyano, $R_2$ represents H and $R_4$ represents tert.butyl.

27. The compound of claim 18 wherein R represents tert.butyl, $R_1$ represents 3-cyano, $R_2$ represents H and $R_4$ represents phenyl.

28. The compound of claim 18 wherein R represents tert. butyl, $R_1$ represents 6-methyl, $R_2$ represents H and $R_4$ represents tert.butyl.

29. The compound of claim 18 wherein R represents tert. butyl, $R_1$ represents 3-bromo, $R_2$ represents 2-methyl and $R_4$ represents tert.butyl.

30. The compound of claim 18 wherein R represents tert.butyl, $R_1$ represents 3-bromo, $R_2$ represents 2-methyl and $R_4$ represents 3,4,5-trimethoxyphenyl.

31. The compound of claim 18 wherein R represents tert.butyl, $R_1$ represents 3-cyano, $R_2$ represents H and $R_4$ represents tert.butyl.

32. The compound of claim 18 wherein R represents tert.butyl, $R_1$ represents 3-cyano, $R_2$ represents H and $R_4$ represents 4-fluorophenyl.

33. The compound of claim 18 wherein R represents tert. butyl, $R_1$ represents 3-bromo, $R_2$ represents 2-methyl and $R_4$ represents phenyl.

34. The compound of claim 18 wherein R represents tert.butyl, $R_1$ represents 3-cyano, $R_2$ represents H and $R_4$ represents 3,4,5-trimethoxyphenyl.

35. The compound of claim 1 which is 4-[3-(3,4-dimethoxy-phenethylamino)-2-hydroxypropoxy]thieno[3,2-c]pyridine-2-carbonitrile.

* * * * *

UNITED STATES PATENT AND TRADEMARK OFFICE
CERTIFICATE OF CORRECTION

PATENT NO. : 4,165,374
DATED : Aug. 21, 1979
INVENTOR(S) : Troxler et al.

It is certified that error appears in the above—identified patent and that said Letters Patent is hereby corrected as shown below:

Column 5, after line 13 and before the table, please insert the following: -- The following compounds of formula Ia are also obtained in a manner analogous to Example 1: --.

Signed and Sealed this

Twenty-fourth Day of June 1980

[SEAL]

Attest:

SIDNEY A. DIAMOND

*Attesting Officer*  *Commissioner of Patents and Trademarks*